(12) United States Patent
Satomi et al.

(10) Patent No.: US 7,238,727 B2
(45) Date of Patent: Jul. 3, 2007

(54) COMPOSITIONS FOR IMPROVING LIPID METABOLISM

(75) Inventors: Susumu Satomi, Miyagi (JP); Hideyuki Doi, Miyagi (JP); Hiromichi Komatsu, Miyagi (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 515 days.

(21) Appl. No.: 10/399,145

(22) PCT Filed: Oct. 12, 2001

(86) PCT No.: PCT/JP01/08991

§ 371 (c)(1),
(2), (4) Date: Apr. 14, 2003

(87) PCT Pub. No.: WO02/30418

PCT Pub. Date: Apr. 18, 2002

(65) Prior Publication Data

US 2003/0183091 A1 Oct. 2, 2003

(30) Foreign Application Priority Data

Oct. 13, 2000 (JP) ............................. 2000-312862

(51) Int. Cl.
*A61K 31/195* (2006.01)
(52) U.S. Cl. ...................................... 514/561
(58) Field of Classification Search .................... None
See application file for complete search history.

(56) References Cited

U.S. PATENT DOCUMENTS

| | | | |
|---|---|---|---|
| 4,042,687 A * | 8/1977 | Gans et al. | ................ 514/21 |
| 4,833,128 A | 5/1989 | Solomon et al. | |
| 4,920,098 A * | 4/1990 | Cotter et al. | .................... 514/2 |
| 5,032,608 A | 7/1991 | Dudrick | |
| 5,242,697 A | 9/1993 | Luca | |

FOREIGN PATENT DOCUMENTS

| | | |
|---|---|---|
| EP | 0 482 715 A1 | 4/1992 |
| EP | 0 483 614 A1 | 5/1992 |
| EP | 0605742 A1 | 7/1994 |
| EP | 0724842 A2 | 8/1996 |
| EP | 0 759 295 A1 | 4/1997 |
| EP | 1 025 844 A1 | 8/2000 |
| JP | 6-24977 | 2/1994 |
| JP | 6-336432 | 12/1994 |
| JP | 9-157163 | 6/1997 |
| WO | WO 88/01872 A1 | 3/1988 |
| WO | WO 97/25972 | 7/1997 |
| WO | WO 00/04870 | 2/2000 |

OTHER PUBLICATIONS

Garrison et al., The Nutrition Desk Reference, published 1985 by Keats Publishing, Inc. (CT), pp. 29-34.*
Pierre Kamoun, TIBS, 17, 1992, pp. 175-176.
Nishihira et al., "Prevention of Fatty Liver and Maintenance of Systemic Valine Depletion Using a Newly Developed Dual Infusion System", Journal of Parenteral and Enteral Nutrition, 1995, pp. 199-203, vol. 19, No. 3.
Komatsu et al., "Amino Acid imbalance anti-cancer therapy and immunity", Database Embase Elsevier Science Publications, 1998, Amsterdam, NL.

* cited by examiner

*Primary Examiner*—Raymond J. Henley, III
(74) *Attorney, Agent, or Firm*—Browdy and Neimark, PLLC

(57) ABSTRACT

This invention aims at providing compositions and foods for improving lipid metabolism which improve the metabolism of lipids and thus are expected to contribute to the prevention and amelioration of hyperlipemia, obesity, atherosclerosis and the like. The invention provides compositions for improving lipid metabolism, compositions for preventing or treating hyperlipemia, compositions for preventing or treating obesity and foods for preventing or ameliorating hyperlipemia and obesity, which contain valine as an active ingredient.

5 Claims, 7 Drawing Sheets

Fig. 7
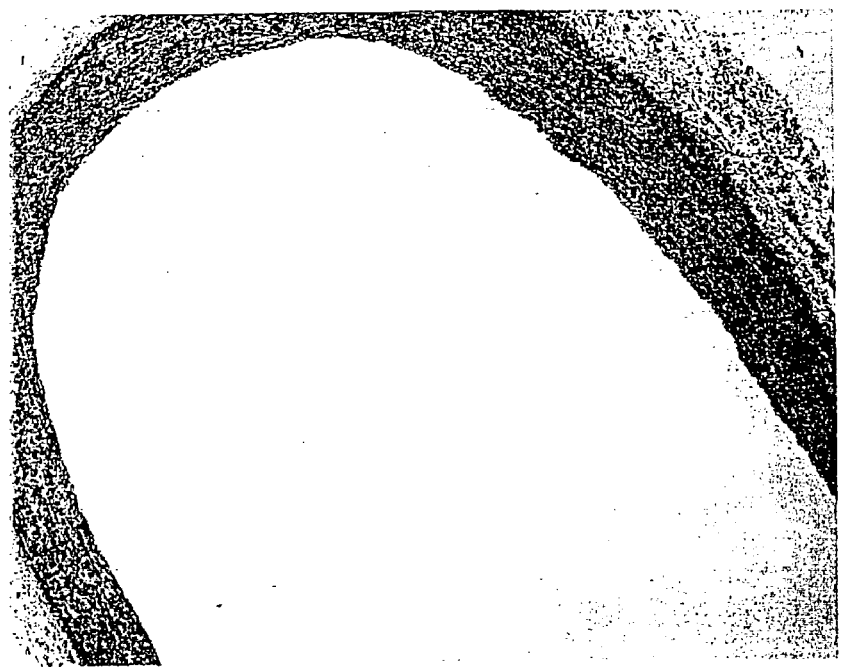
(a) CONTROL GROUP
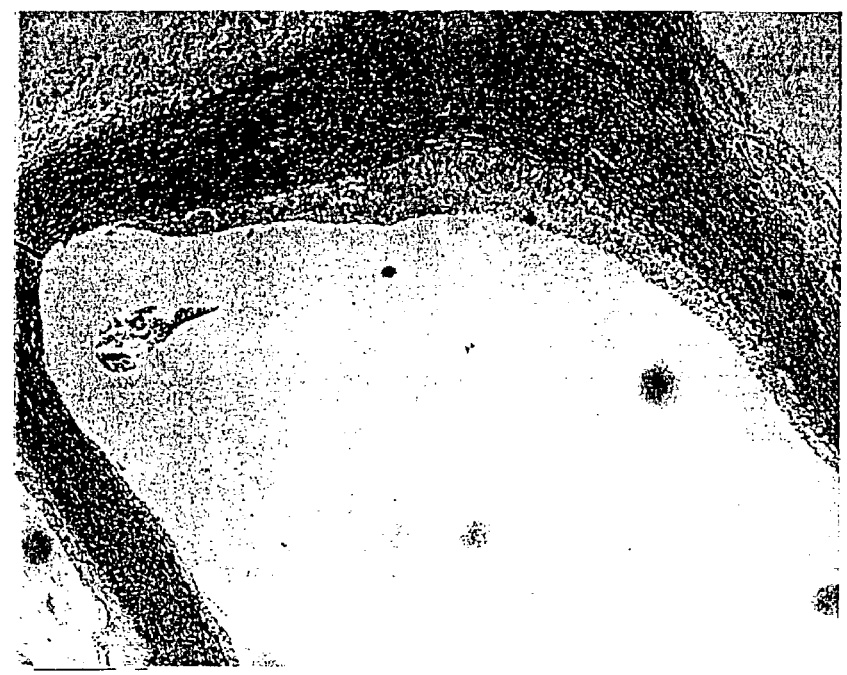
(b) VALINE GROUP

COMPOSITIONS FOR IMPROVING LIPID METABOLISM

TECHNICAL FIELD

This invention relates to compositions for improving lipid metabolism which improve the metabolism of lipids and thus can be expected to contribute to the prevention and amelioration of obesity, hyperlipemia, atherosclerosis and the like. It further relates to compositions for preventing or treating hyperlipemia and foods for preventing or ameliorating hyperlipemia. It still further relates to compositions for preventing or treating obesity and foods for preventing or ameliorating obesity.

BACKGROUND ART

In recent years, lipid intake has been increasing in Japan with the tendency toward improved and Western-style eating habits, which brings about a problem of excessive fat intake. The excessive fat intake causes obesity and an increase in the serum lipid level and consequently heightens the risk of the onset of various complications thereof (for example, circulatory diseases, in particular, coronary and cerebral vascular accidents and life-style related diseases such as certain cancers including breast cancer and colon cancer). Thus, it becomes a serious social problem from the viewpoint of maintaining and improving national health.

It has been pointed out that an increase in the levels of cholesterol in the blood is one of the risk factors of the onset of circulatory diseases. Recently, high concentrations of triacylglycerol (triglyceride) in the blood have also attracted attention as another risk factor independent from those of cholesterol.

Hyperlipemia means a condition wherein the blood cholesterol concentration and/or the blood triacylglycerol (i.e., one of neutral fats) concentration are increased. Hypercholesterolemia (hyper-β-lipoproteinemia) with an increase in the blood cholesterol level is caused mainly by an increase in the low-density lipoprotein (LDL, β-lipoprotein) to a level which is well known as one of the risk factors for atherosclerosis. It is also pointed out that the excessive lipid intake results in a continuous increase in the blood triacylglycerol concentration and, in turn, causes the onset of hypertriacylglycerolemia which is likely to induce atherosclerotic diseases such as hypertension and ischemic heart disease.

Moreover, an excess in stored energy due to the excessive lipid intake causes obesity. Obesity, which is defined as a condition with an abnormal increase in adipose in the body, is associated with an increase in visceral adipose and/or panniculus adipose. Classifications of obesity are: obesity in the upper half of the body; obesity in the lower half of the body; central obesity; peripheral obesity; visceral obesity; panniculus obesity and the like depending on the part of the body with the increased amount of adipose.

Also, obesity is regarded as one of the causative factors of life-style related diseases such as diabetes, hyperlipemia, hypertension, fatty liver, atherosclerosis, gout, myocardial infarction and angina. People suffering from these diseases sometimes develop complications depending on the areas of adipose deposition. It has been clarified that visceral adipose deposition is associated with the highest risk.

Methods of treating hyperlipemia and obesity include dietotherapy and chemotherapy which are usually combined with kinesitherapy and health guidance. However, these existing therapies suffer from various drawbacks: it is highly difficult to continue these treatments over a long period of time; they are less convenient; and there is a fear of side effects.

The percentage of patients with atherosclerosis in the total population of Japan has been increasing constantly and it is known that abnormal lipid metabolism is deeply involved in the formation of atherosclerosis.

It has been known that valine, which is one of the essential amino acids, is usable in therapeutic agents for liver regeneration (WO96/00059) and therapeutics for hepatic diseases (WO99/16433). However, it has neither been reported nor suggested so far to use valine in improving lipid metabolism or preventing, ameliorating or treating hyperlipemia, obesity or atherosclerosis.

DISCLOSURE OF THE INVENTION

An object of the present invention is to provide compositions for improving lipid metabolism which improve the metabolism of lipids and thus are expected to contribute to the prevention and amelioration of hyperlipemia, obesity (particularly visceral obesity), atherosclerosis and the like, without suffering from any of the above-described problems.

Another object of the present invention is to provide compositions which are usable in the prevention and treatment of hyperlipemia, obesity and atherosclerosis. Another object of the present invention is to provide foods which can be used to assist in the prevention and amelioration of hyperlipemia and obesity.

Based on the fact that an increase in adipose can be inhibited by administering valine together with a high-fat diet to rats, the present inventors have found that valine has the effect of promoting β-oxidation of lipids and inhibiting increase in adipose, thereby completing the present invention.

Accordingly, the present invention provides a composition for improving lipid metabolism, which contains valine as an active ingredient.

The composition according to the present invention may be a composition substantially containing valine alone as an active ingredient.

The present invention further provides a composition for preventing or treating hyperlipemia, which contains valine as an active ingredient.

The present invention further provides a composition for preventing or treating obesity, which contains valine as an active ingredient.

The present invention still further provides a composition for preventing or treating atherosclerosis, which contains valine as an active ingredient.

Furthermore, the present invention provides a food for improving lipid metabolism, which contains valine as an active ingredient.

The present invention further provides a food for preventing or ameliorating hyperlipemia, which contains valine as an active ingredient.

The present invention further provides a food for preventing or ameliorating obesity, which contains valine as an active ingredient.

The present invention still further provides a food for preventing or ameliorating atherosclerosis, which contains valine as an active ingredient.

It is preferable that the above-described foods are functional foods.

In the compositions or foods according to the present invention, it is preferable that the valine is L-valine.

BRIEF DESCRIPTION OF THE DRAWINGS

In FIG. 1, an open bar stands for a 3% casein+8.4% lard group (n=3), a horizontally striped bar stands for a 3% valine+8.4% lard group (n=3), and a shaded bar stands for a normal food group (n=3). Each bar shows the mean±standard deviation.

In FIG. 2, an open bar stands for a 3% casein+8.4% lard group (n=1), a horizontally striped bar stands for a 3% valine+8.4% lard group (n=1), and a shaded bar stands for a normal food group (n=1).

In FIG. 3, an open bar stands for a 3% casein+8.4% lard group (n=3), a horizontally striped bar stands for a 3% valine+8.4% lard group (n=3), and a shaded bar stands for a normal food group (n=3). Each bar shows the mean±standard deviation.

In FIG. 4, an open bar stands for a 3% casein+8.4% lard group (n=3), a horizontally striped bar stands for a 3% valine+8.4% lard group (n=3), and a shaded bar stands for a normal food group (n=3). Each bar shows the mean±standard deviation.

In FIG. 5, an open bar stands for a 3% casein+8.4% lard group (n=3), a horizontally striped bar stands for a 3% valine+8.4% lard group (n=3), and a shaded bar stands for a normal food group (n=3). Each bar shows the mean±standard deviation.

In FIG. 6, an open bar stands for a 3% casein+8.4% lard group (n=3), a horizontally striped bar stands for a 3% valine+8.4% lard group (n=3), and a shaded bar stands for a normal food group (n=3). Each bar shows the mean±standard deviation.

FIG. 7a is a micrograph (×100) of an HE stained section of the aorta in the chest of a control rabbit; and FIG. 7b is a micrograph (×100) of an HE stained section of the aorta in the chest of a valine-administered rabbit.

BEST MODE FOR CARRYING OUT THE INVENTION

Figure 1:
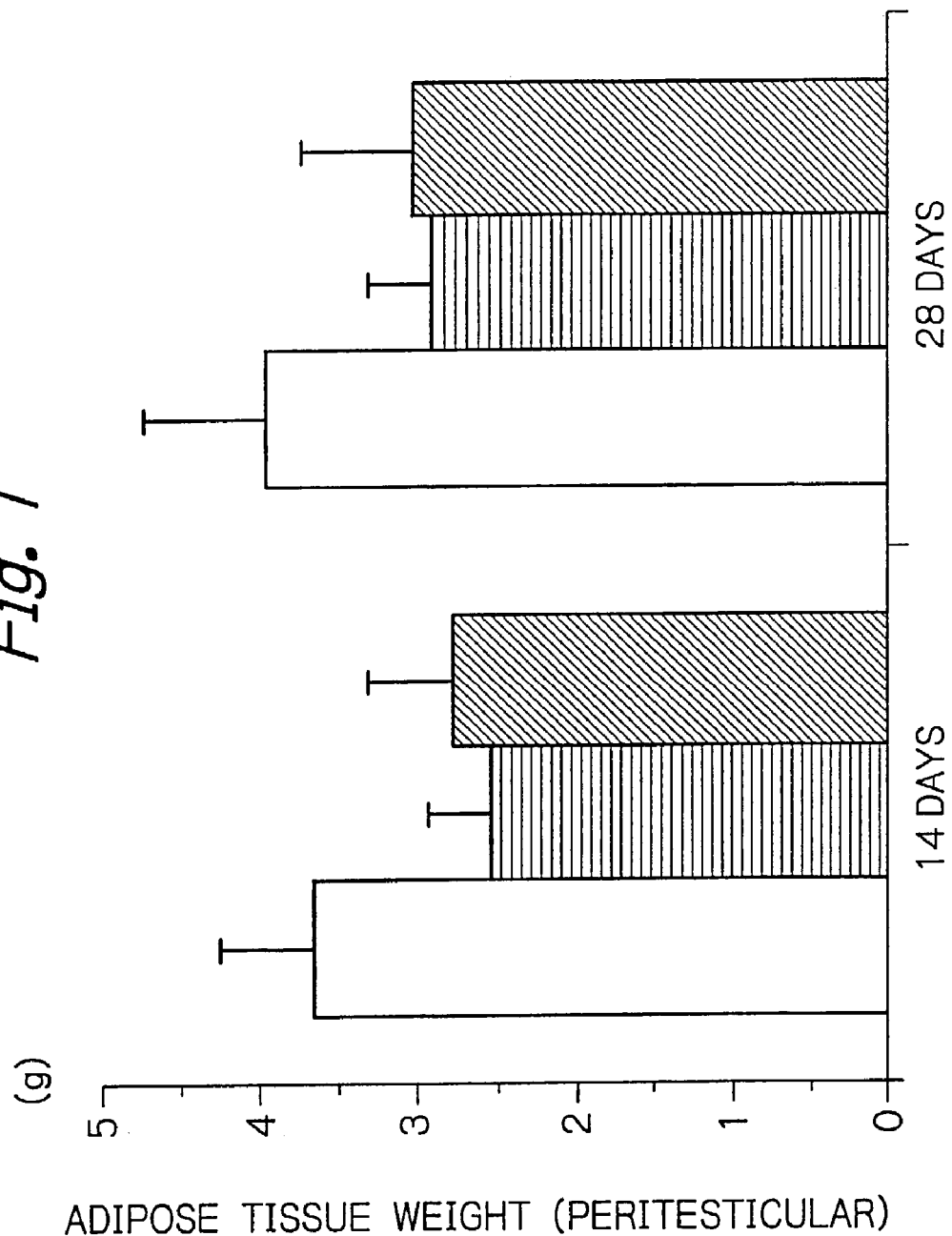
FIG. 1 is a graph showing the mean of the peritesticular adipose tissue weight of the rats of each group.

As the valine to be used in the present invention, marketed products, synthetic products and the like can be arbitrarily employed without limiting the production method. Although D-, L- and DL-valines are all usable, it is particularly preferable to use L-valine.

The compositions for improving lipid metabolism according to the present invention exhibit an effect of improving the lipid metabolism of animals (for example, humans, rabbit and mouse) and thus are expected to exert effects of preventing, treating or ameliorating hyperlipemia (such as hypertriacylglycerolemia and hypercholesterolemia), obesity (such as visceral obesity and panniculus obesity, particularly visceral obesity), visceral adipose tissue syndrome and the like. It is also expected that these compositions contribute to the prevention, amelioration and the like of complications of the above diseases (circulatory diseases such as atherosclerosis and hypertension, life-style related diseases such as certain cancers including breast cancer and colon cancer).

The compositions for preventing or treating hyperlipemia and the foods for preventing or ameliorating hyperlipemia according to the present invention are expected to be effective in preventing, treating or ameliorating hyperlipemia. These compositions and foods are also expected to contribute to the prevention, amelioration and the like of various complications accompanying the same.

The compositions for preventing or treating obesity and the foods for preventing or ameliorating obesity according to the present invention are expected to be effective in preventing, treating or ameliorating obesity (particularly visceral obesity), visceral adipose tissue syndrome and the like. These compositions and foods are also expected to contribute to the prevention, amelioration and the like of various complications accompanying the same.

In the case of administering the compositions for improving lipid metabolism, the compositions for preventing or treating hyperlipemia or the compositions of preventing or treating obesity according to the present invention to a living body, the administration can be made either orally or parenterally (for example, rectally, subcutaneously, intraspinally, intramuscularly, intravenously, intra-arterially and transdermally). Oral or intravenous administration is preferable.

These compositions according to the present invention may be formulated into preparations of appropriate dosage forms, for example, tablets, dusts, granules, fine subtilaes, pills, capsules, troches, chewable tablets, solutions, emulsions, suspensions, suppositories and syrups. These preparations may be produced by using pharmaceutically acceptable carriers, excipients, additives and the like.

In the case of intravenous administration, it is preferable to use the compositions according to the present invention in the form of solutions, emulsions or suspensions. Solutions can be prepared by using solvents such as purified water, physiological saline, alcohols (such as ethanol, propylene glycol, glycerol and polyethylene glycol) and triacetin. These preparations may further contain auxiliary agents such as preservatives, moistening agents, emulsifiers, dispersants and stabilizers.

Solid preparations such as tablets, pills, dusts, granules, fine subtilaes, troches and chewable tablets can be produced in a conventional manner with the use of, for example, carriers (such as sodium bicarbonate, calcium carbonate, starch, sucrose, mannitol and carboxymethylcellulose) and additives (such as calcium stearate, magnesium stearate and glycerol). It is also possible to produce enteric preparations by spraying solutions of enteric substances (such as cellulose acetate phthalate, hydroxypropylmethylcellulose phthalate, polyvinyl alcohol phthalate, styrene-maleic anhydride copolymer and methacrylic acid-methyl methacrylate copolymer) in organic solvents or water to thereby form enteric coatings. The pharmaceutically acceptable carriers include other auxiliary agents, aromatic agents, stabilizers and preservatives commonly employed in the art if needed. Furthermore, the compositions of the present invention may be used together with transfusion preparations or added to other transfusion preparations.

In the case of being used as medicines, the compositions according to the present invention may be administered in various doses depending on the sex, body type, constitution, age and condition of the patient, dosage form and the like. In general, the dose may be appropriately selected to give from 0.1 to 50 g/day, preferably from 1 to 25 g/day, of valine as an active ingredient to an adult. The administration frequency varies depending on the condition of the patient, dosage form or the like. It is adequate to administer from once to several times per day.

The foods for preventing or ameliorating hyperlipemia and the foods for preventing or ameliorating obesity according to the present invention may be either foods substantially containing valine on its own or products prepared by adding valine directly to existing foods, drinks or the like. For example, valine can be added directly to confectioneries (such as chewing gum, candy, jelly, gummy candy, cookie, biscuit and chocolate), soft drinks (such as juice), processed milk products (such as cheese, butter and yogurt), processed agricultural products (such as ice cream and ham), processed fish products (such as chikuwa and hanpen), noodles (such as soba and udon), processed wheat flour products (such as bread and cake), canned foods, seasonings (such as salt, pepper, sugar and synthetic sweetener) and the like. It is also possible to add valine during the manufacturing process of these food products. To produce processed foods containing valine, use can be made of conventional food processing methods. To add valine to foods, the valine may be used in the form of either a solid (such as powder, granules and fine subtilaes) or a liquid. The foods for preventing or ameliorating hyperlipemia and the foods for preventing or ameliorating obesity according to the present invention are applicable as specified health foods, functional foods or health foods for preventing or ameliorating hyperlipemia or obesity. The term "functional foods" means foods containing components having biological regulatory functions. The functions of individual food products can be indicated under the approval by the Ministry of Health, Labour and Welfare.

It is generally preferable that the foods according to the present invention contain from about 0.1 to 50 g of valine per 100 g. In the case of human adults, it is generally favorable to administer such a food so as to provide a daily valine intake of 1 to 25 g, though the recommended intake level varies depending on the sex, body type, constitution and age of the subject, other foods consumed and the like. It is adequate to administer from once to several times per day.

The compositions for improving lipid metabolism according to the present invention are efficacious on animals other than humans. Thus, these compositions can be used in order to prevent excessive body fat accumulation and improve meat qualities of, for examples, domestic animals such as cattle and pig and cultivated fishes such as yellow tail and sea bream. Moreover, these compositions are usable in the prevention or amelioration of hyperlipemia or obesity in dogs and cats; it can also be used for controlling the health of these pets.

The compositions for improving lipid metabolism according to the present invention may be given to animals by, for example, adding it to animal feeds, fish feeds or pet foods. The form and production method of these feeds or pet foods can be arbitrarily selected by those skilled in the art without restriction. In general, the desired feeds or pet foods can be easily produced by preliminarily adding valine to fats or oils employed as raw materials or adding valine in an appropriate manner in the course of production. In the case of the feeds and pet foods, it is generally favorable to add from about 0.1 to 50 g of valine per 100 g, though the addition level varies from animal to animal.

EXAMPLE

Hereinbelow, the present invention will be illustrated in greater detail with reference to the following Examples, which should not be construed as limiting the scope of the present invention.

Example 1

To evaluate the effects of valine on lipid metabolism, the effects of the administration of L-valine containing feeds were examined on matured rat models fed with high-fat diets.

I. Experimental Method

18 Crj:CD(SD) IGS male rats aged 12 weeks (body weight: 420 to 464 g, 443 g on average) were pre-fed for 5 days (not more than 4 animals/cage, temperature: 20 to 26° C., humidity: 30 to 70%, illumination: 8:00 to 20:00). During the pre-feeding period, the animals were maintained on a feed (constant feeding) and water (using a water supplier) as desired.

After the completion of the pre-feeding, the animals were divided into 6 groups depending on feed and administration period. Rats of valine+lard groups were fed with a solid feed prepared by adding 8.4% lard (CAMERIA: manufactured by Romi Smilfood B. V.) and 3.0% L-valine (JP, manufactured by Ajinomoto Co., Inc.) to a conventional feed (CMF: manufactured by Oriental Yeast Co., Ltd.) for 2 or 4 weeks. Animals of casein+lard groups (i.e., control groups) were fed with a solid feed prepared by adding 8.4% lard and 3.0% milk-origin casein (manufactured by Wako Pure Chemical Industries, Ltd.) to the conventional feed (CMF: manufactured by Oriental Yeast Co., Ltd.) for 2 or 4 weeks. Animals of normal food groups were fed with a solid feed which was the conventional feed (CMF: manufactured by Oriental Yeast Co., Ltd.) for 2 or 4 weeks. During the experimental period, the rats of each group were maintained on the feed (constant feeding) and water (using a water supplier) as desired. Each group had 3 rats which were fed in a single cage (temperature: 20 to 26° C., humidity: 30 to 70%, illumination: 8:00 to 20:00) throughout the experimental period.

After 2 or 4 weeks, the blood samples of the animals of each group were collected from the abdominal aorta and then the animals were sacrificed by bleeding under etherization followed by autopsy. As intraperitoneal adipose tissue, the adipose tissue around the left testis and epididymis was weighed. The collected blood samples were subjected to a serobiochemical examination and the like.

22 days after the initiation of the experiment, one rat of each of the 4 weeks-feeding groups was subjected to the abdominal CT scanning (slice width: 5 mm) under anesthesia with Nembutal. From the CT image thus obtained, the intraperitoneal adipose tissue area was determined as the mean of the intraperitoneal adipose-containing areas in posterior 4 slices from the sites where no kidney was observed.

II. Results (1) Adipose Tissue Weight

FIG. 1 shows the mean of the peritesticular adipose tissue weight (around the left testis and epididymis) of the rats of each group. In the 2 weeks-feeding groups, the peritesticular adipose tissue weight (g) of the casein+lard group was 3.66±0.60 (mean±standard deviation, the same will apply hereinafter), while those of the valine+lard group and the normal food group were respectively 2.55±0.38 and 2.78±0.54. A comparison of the data of these groups indicates that the mean adipose tissue weight of the valine+lard group was about 0.70 times as much as that of the casein+lard group. Namely, the adipose tissue weight of the valine+lard group was less by 30% than that of the casein+lard group. Also, the adipose tissue weight of the valine+lard group was smaller than that of the normal food group.

In the 4 weeks-feeding groups, the adipose tissue weight (g) of the casein+lard group was 3.97±0.78, while those of the valine+lard group and the normal food group were respectively 2.92±0.40 and 3.03±0.70. A comparison of the data of these groups indicates that the mean adipose tissue weight of the valine+lard group was about 0.74 times as much as that of the casein+lard group. Namely, the adipose tissue weight of the valine+lard group was less by 26% than that of the casein+lard group. Also, the adipose tissue weight of the valine+lard group was smaller than that of the normal food group.

In the 2 weeks-feeding groups, the average daily feed intakes (g) per animal of the casein+lard group, the valine+lard group and the normal food group were: respectively 15.7, 18.0 and 16.3 on day 1; 28.7, 24.3 and 26.3 on day 7; and 25.0, 24.7 and 23.3 on day 14 (the day of autopsy). Namely, similar data were observed among these 3 groups of 2 weeks-feeding. In the 4 weeks-feeding groups, the average daily feed intakes (g) per animal of the casein+lard group, the valine+lard group and the normal food group were: respectively 13.0, 18.7 and 16.7 on day 1; 26.3, 25.3 and 27.7 on day 7; 25.3, 25.0 and 26.7 on day 14; 25.7, 24.3 and 25.3 on day 21; and 24.0, 23.7 and 27.0 on day 28 (the day of autopsy). Namely, similar data were observed among these 3 groups of 4 weeks-feeding.

As discussed above, the increase in the adipose tissue weight was inhibited in the rats fed with the feed containing valine, both in the 2-weeks feeding group and the 4 weeks-feeding group, though the feed intake data of the groups were almost the same.

(2) Intraperitoneal Adipose Tissue Area

Figure 2:
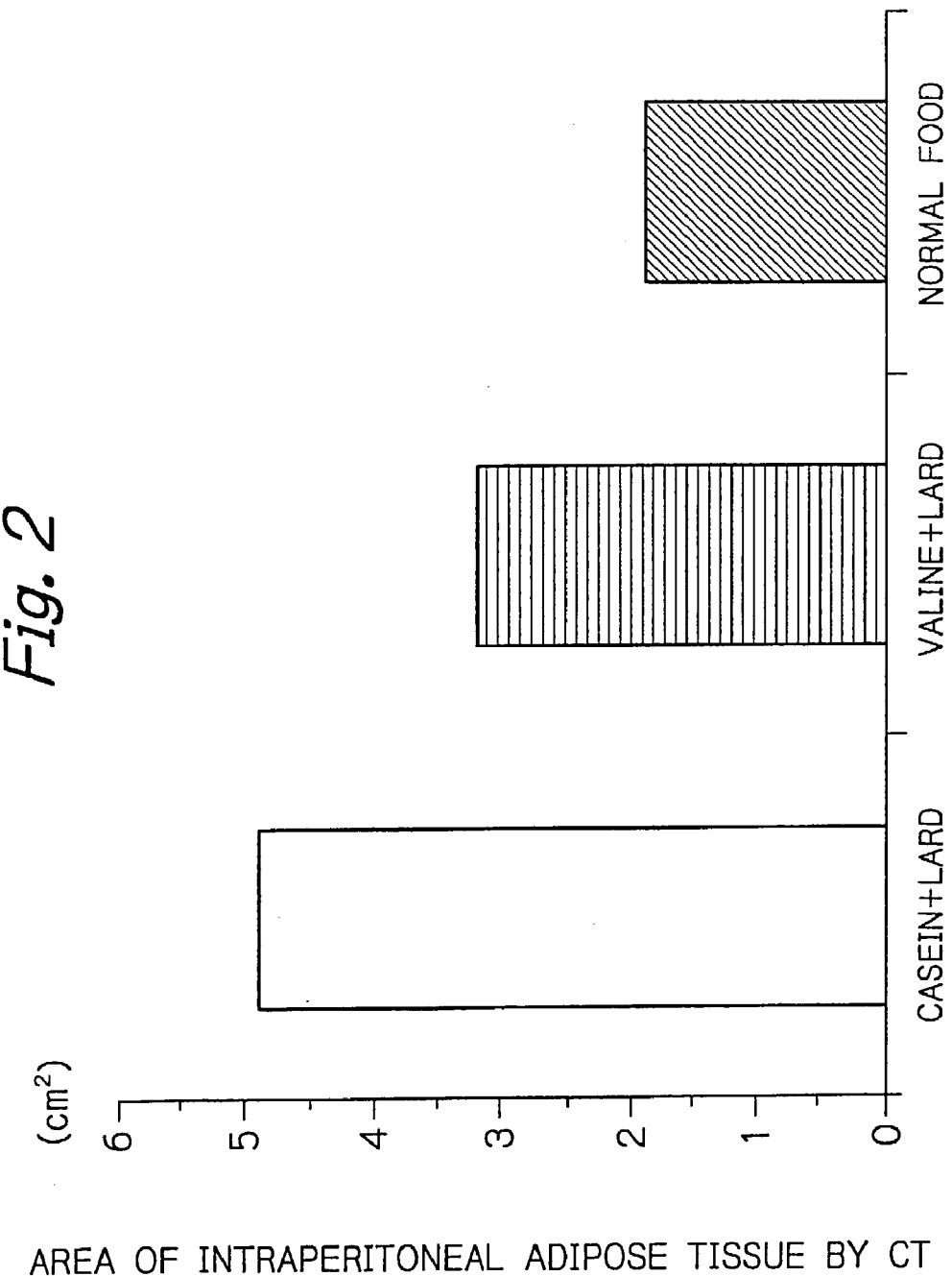
FIG. 2 is a graph showing the area of the intraperitoneal adipose tissue of a rat of each 4 weeks-feeding group calculated from the CT image.

FIG. 2 shows the area of the intraperitoneal adipose tissue of a rat of each 4 weeks-feeding group calculated from the CT images of the abdominal part of the rat. The intraperitoneal adipose tissue areas ($cm^2$) of the rats of the casein+lard group, the valine+lard group and the normal food group were respectively 4.9, 3.2 and 1.9. The intraperitoneal adipose tissue of the valine+lard group was about 0.65 times as much as that of the casein+lard group. As discussed above, the feed intake data of the groups were almost the same. However, the increase in the intraperitoneal adipose tissue area was more inhibited in the rats fed with the feed containing valine than in the casein+lard group.

(3) Serobiochemical Examination (i) Triacylglycerol

Figure 3:
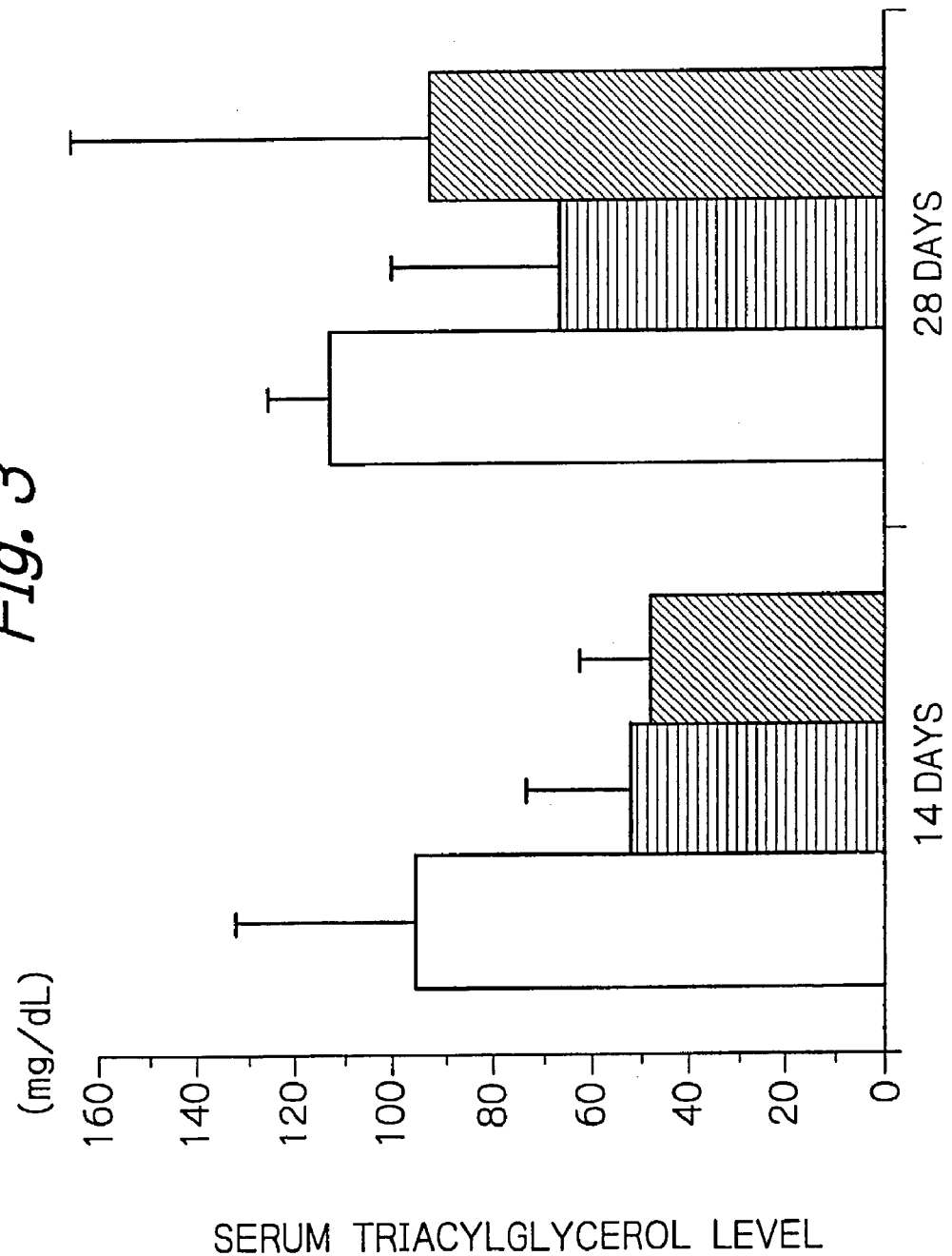
FIG. 3 is a graph showing the mean of the serum triacylglycerol level of the rats of each group.

FIG. 3 shows the mean serum triacylglycerol level of the rats of each group. In the 2 weeks-feeding groups, the mean triacylglycerol levels (mg/dL) of the casein+lard group, the valine+lard group and the normal food group were respectively 95.7±36.7, 52.0±21.9 and 48.3±14.7. Namely, the mean triacylglycerol level (mg/dL) of the valine+lard group was about 0.54 times as much as that of the casein+lard group.

In the 4 weeks-feeding groups, the mean triacylglycerol levels of the casein+lard group, the valine+lard group and the normal food group were respectively 113.7±13.2, 67.7±33.5 and 94.0±73.3. Namely, the mean triacylglycerol level of the valine+lard group was about 0.60 times as much as that of the casein+lard group.

(ii) Free Fatty Acid

Figure 4:
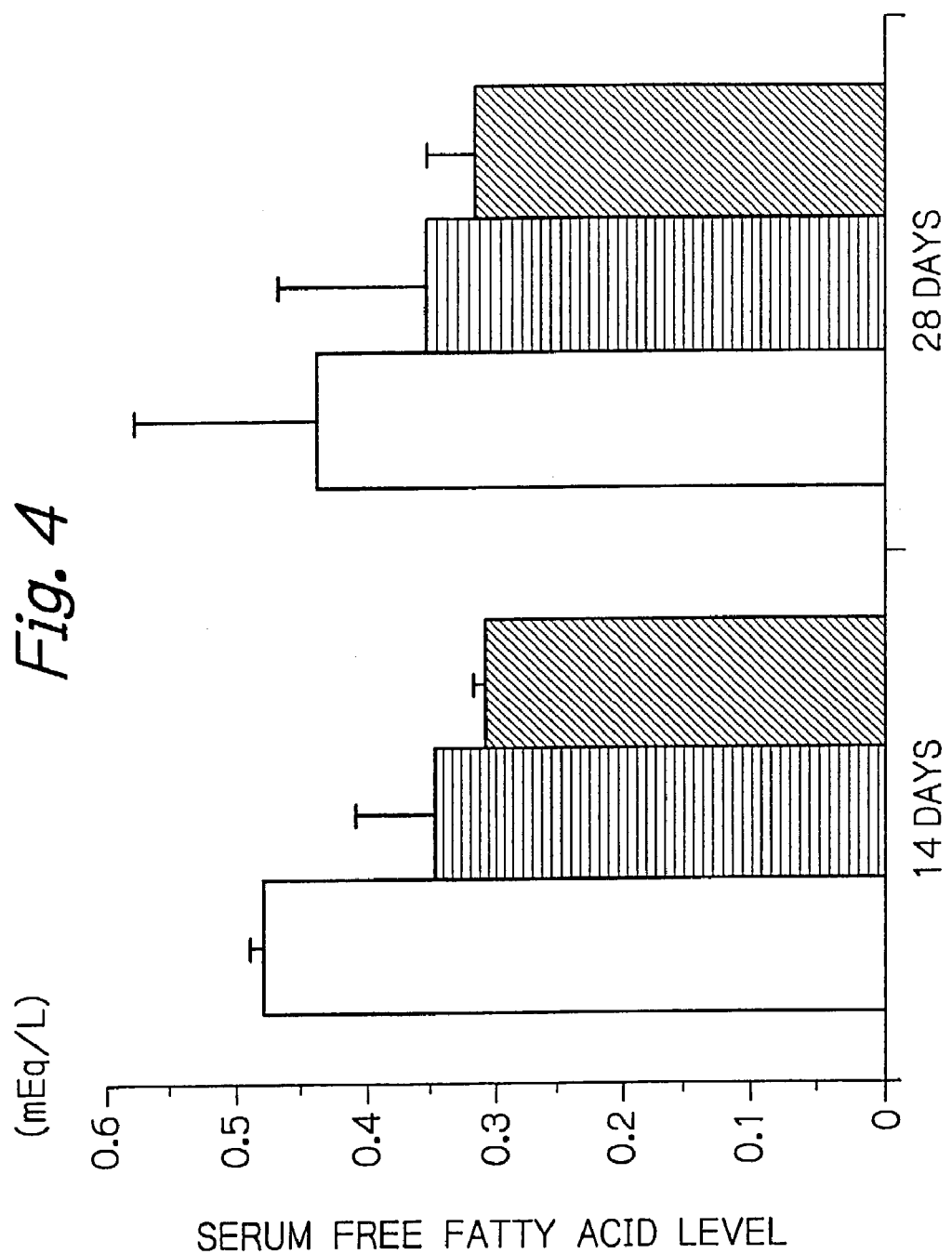
FIG. 4 is a graph showing the mean of the serum free fatty acid level of the rats of each group.

FIG. 4 shows the mean serum free fatty acid level of the rats of each group. In the 2 weeks-feeding groups, the mean free fatty acid levels (mEq/L) of the casein+lard group, the valine+lard group and the normal food group were respectively 0.48±0.01, 0.35±0.06 and 0.31±0.01. Namely, the mean free fatty acid level of the valine+lard group was about 0.73 times as much as that of the casein+lard group.

In the 4 weeks-feeding groups, the mean free fatty acid levels of the casein+lard group, the valine+lard group and the normal food group were respectively 0.44±0.14, 0.36±0.11 and 0.32±0.04. Namely, the mean free fatty acid level of the valine+lard group was about 0.82 times as much as that of the casein+lard group.

(iii) Lipid Peroxide

Figure 5:
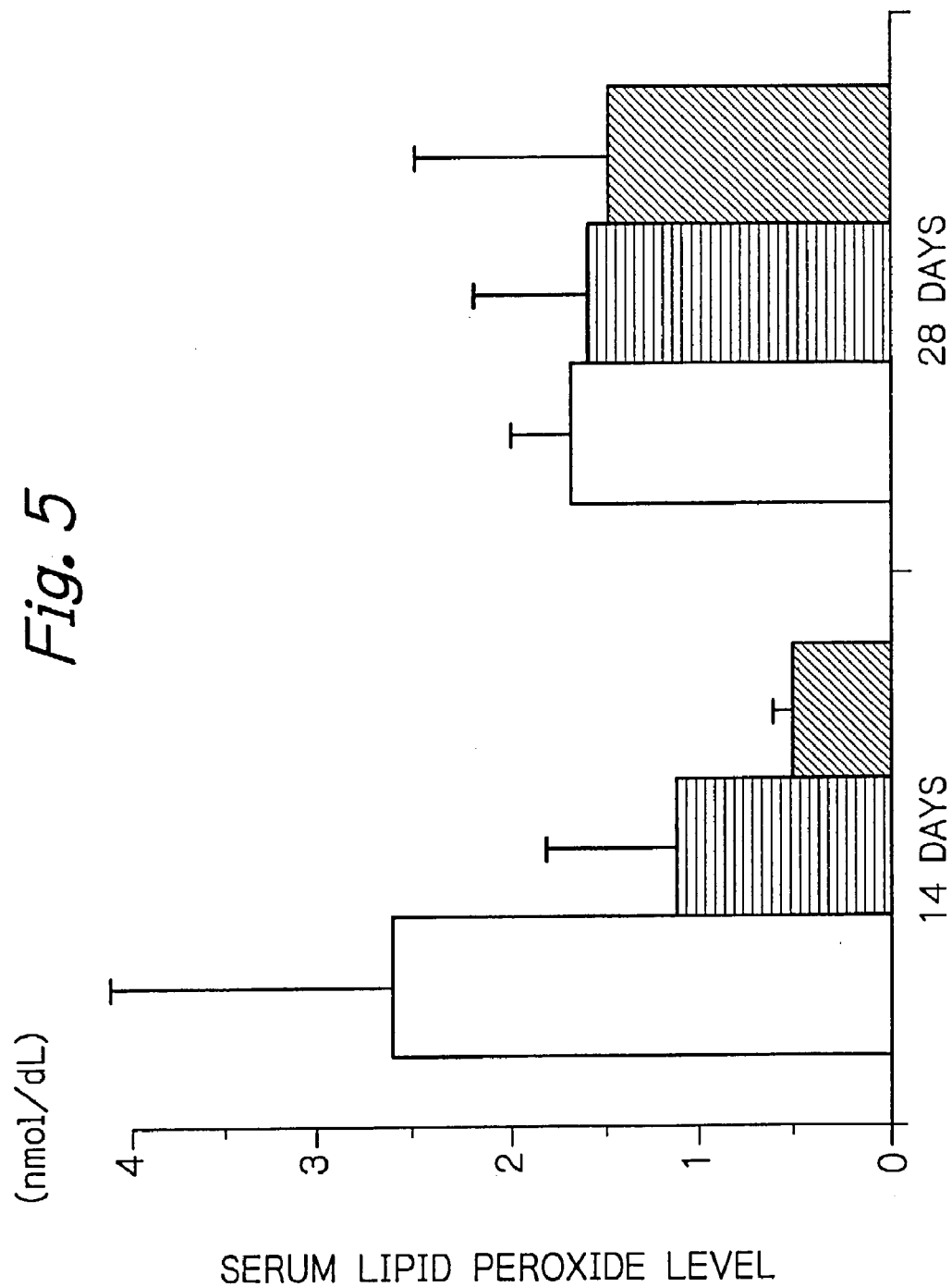
FIG. 5 is a graph showing the mean of the serum lipid peroxide level of the rats of each group.

FIG. 5 shows the mean serum lipid peroxide level of the rats of each group. In the 2 weeks-feeding groups, the mean lipid peroxide levels (nmol/dL) of the casein+lard group, the valine+lard group and the normal food group were respectively 2.6±1.5, 1.1±0.7 and 0.5±0.1. Namely, the mean lipid peroxide level of the valine+lard group was about 0.42 times as much as that of the casein+lard group.

(iv) β-Lipoprotein

Figure 6:
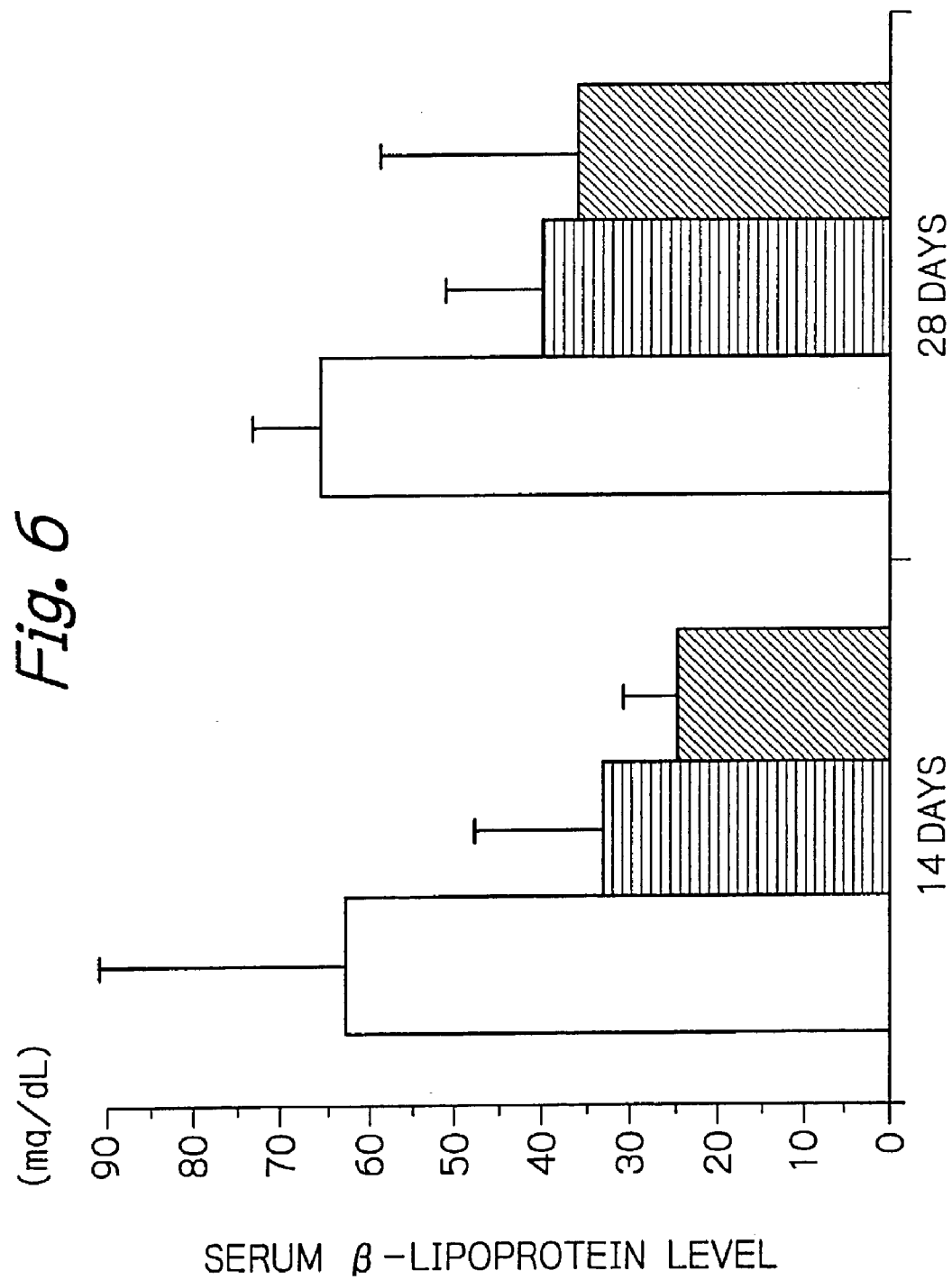
FIG. 6 is a graph showing the mean of the serum β-lipoprotein level of the rats of each group.

FIG. 6 shows the mean serum β-lipoprotein level of the rats of each group. In the 2 weeks-feeding groups, the mean β-lipoprotein levels (mg/dL) of the casein+lard group, the valine+lard group and the normal food group were respectively 63.0±27.8, 33.3±14.5 and 25.0±6.0. Namely, the mean β-lipoprotein level of the valine+lard group was about 0.53 times as much as that of the casein+lard group.

In the 4 weeks-feeding groups, the mean β-lipoprotein levels of the casein+lard group, the valine+lard group and the normal food group were respectively 66.0±7.8, 41.0±10.8 and 36.3±23.1. Namely, the mean β-lipoprotein level (mg/dL) of the valine+lard group was about 0.62 times as much as that of the casein+lard group.

As described above, the valine+lard groups showed decreases in the lipid items (such as triacylglycerol, β-lipoprotein and free fatty acid) in the serobiochemical examination. Also, the valine+lard group showed a decrease in lipid peroxides which are considered one of the causative factors of various vascular lesions and have been clarified as being carcinogenic.

Example 2

In order to evaluate the efficacy of valine on atherosclerosis and fatty liver, an L-valine containing feed was administered to a rabbit atherosclerotic model and its effect was investigated.

I. Experimental Method

Nine New Zealand White male rabbits aged 8 weeks (average body weight, 2.06 kg) were divided into three groups (n=3) by feed and fed for 13 weeks (temperature, 20 to 26° C.; humidity, 30 to 70%; illumination, 8:00 to 20:00). The untreated group was given an ordinary feed (NOSAN feed for laboratory animals, LABOR STOCK, manufactured by Nihon Nosan Kogyo, K.K.). As for the atherosclerotic model, the control group was given the ordinary feed plus 0.2% cholesterol (manufactured by Wako Pure Chemical Industries, Ltd.), and the valine group was given the ordinary feed plus 0.2% cholesterol plus 3.0% L-valine (JP, manufactured by Ajinomoto Co., Inc.). Throughout the experiment, the rabbits of each group were maintained on the feed (constant feeding) and water (using a water supplier) as desired.

After 13 weeks, blood samples were collected from the abdominal aorta of the animals of each group under etherization and the animals were then sacrificed by bleeding. By subsequent autopsy, the degree of atherosclerotic lesion (plaque formation) in thoracic aorta and the degree of fatty liver were compared. Sections of the thoracic aorta and the liver were also prepared and examined histopathologically for intimal thickening and the formation of fat droplets.

II. Results (1) Plaque Formation

Table 1 shows the result of evaluation of plaque formation in specimens of the aortic arch; in Table 1, "+" denotes visible slight plaque formation, "++" denotes visible moderate plaque formation, and "−" denotes no visible plaque formation. In the three cases of the control group, moderate plaque formation was observed in the branch and nearby areas. In the valine group, no plaque formation was visible, or plaque formation was visible but to a lesser extent than in the control group.

TABLE 1

Result of Evaluation of Plaque Formation in Specimens of Aortic Arch

|  | 1 | 2 | 3 |
| --- | --- | --- | --- |
| Control group | ++ | ++ | ++ |
| Valine group | − | − | + |

(2) Intimal Thickening

Sections of the thoracic aorta were HE stained (hematoxylin-eosin stained). The control group had visible intimal thickening (FIG. 7a) but in the valine group, intimal thickening was hardly visible (FIG. 7b).

(3) Fatty Liver

Observation of the liver with the naked eye showed that visible yellowing of the liver (fatty liver) occurred in the control group in proportion to the level in the serum lipid test. In the valine group, no yellowing of the liver was observed, or yellowing of the liver was visible but to a lesser extent than in the control group.

When liver sections were HE stained, hepatocytes of the control group were filled with fat droplets to become swollen but in the valine group, hepatocytes contained such a small number of fat droplets that they experienced no visible swelling.

Thus, it was demonstrated that the degrees of plaque formation, intimal thickening and fatty liver were smaller in the valine group than in the control group (atherosclerotic model). Valine is therefore anticipated to be useful in the prevention or treatment of atherosclerosis and in the prevention or treatment of fatty liver.

INDUSTRIAL APPLICABILITY

As discussed above, the administration of a valine-containing feed to rats fed with the high-fat diet resulted in decreases in lipid items in the serobiochemical examination. Moreover, inhibition of an increase in the intraperitoneal adipose tissue area was observed in the CT scanning photographic images. In addition, inhibition of the increase in peritesticular adipose tissue weight (i.e., visceral adipose) was observed.

Therefore, it is suggested that the compositions or foods according to the present invention have an effect of improving the lipid metabolism and, therefore, are expected to be highly useful in clinical medicine. Compared with the conventional ones, furthermore, the compositions or foods of the present invention are regarded as useful products for preventing or ameliorating hyperlipemia, obesity (particularly visceral obesity), atherosclerosis or the like, seemingly carry less risk of side effects and can easily be taken over a long period of time.

The invention claimed is:

1. A method for improving lipid metabolism in a patient in need thereof, including at least one of reducing atherosclerosis, inhibiting an increase in intraperitoneal adipose tissue and inhibiting visceral obesity, inhibiting visceral adipose tissue syndrome, and inhibiting fatty liver, comprising administering valine to said patient in need of said improving, in an amount sufficient therefor, wherein said valine is substantially entirely L-valine and substantially entirely free of other amino acids.

2. The method of claim 1 wherein said patient is a patient diagnosed as suffering from atherosclerosis.

3. The method of claim 1, wherein said valine is administered together with a pharmaceutical carrier.

4. The method of claim 1, wherein said valine is administered at a dosage rate of 0.1 to 50 g/day.

5. The method of claim 1, wherein said valine is administered at a dosage rate of 1 to 25 g/day.

* * * * *